(12) United States Patent
El Boutachfaiti et al.

(10) Patent No.: US 8,563,276 B2
(45) Date of Patent: Oct. 22, 2013

(54) METHOD OF ENZYME CLEAVAGE OF POLYSACCHARIDES DERIVED FROM ALGAE

(75) Inventors: Redouan El Boutachfaiti, Lille (FR); Patrice Pheulpin, Amiens (FR); Bernard Courtois, Amiens (FR); Josiane Courtois-Sambourg, Amiens (FR)

(73) Assignee: Universite de Picardie Jules Verne (FR)

( * ) Notice: Subject to any disclaimer, the term of this patent is extended or adjusted under 35 U.S.C. 154(b) by 423 days.

(21) Appl. No.: 12/664,743

(22) PCT Filed: Jun. 23, 2008

(86) PCT No.: PCT/FR2008/000881
§ 371 (c)(1),
(2), (4) Date: May 12, 2010

(87) PCT Pub. No.: WO2009/016275
PCT Pub. Date: Feb. 5, 2009

(65) Prior Publication Data
US 2010/0261894 A1    Oct. 14, 2010

(30) Foreign Application Priority Data

Jun. 22, 2007    (FR) .................... 07 04494

(51) Int. Cl.
*C12P 19/12*    (2006.01)
*C12N 9/88*    (2006.01)

(52) U.S. Cl.
USPC .......................... 435/100; 435/232

(58) Field of Classification Search
None
See application file for complete search history.

(56) References Cited

PUBLICATIONS

Lahaye et al Carbohydrate research 1997, 304, pp. 325-333.*

\* cited by examiner

*Primary Examiner* — Tekchand Saidha
*Assistant Examiner* — Md. Younus Meah
(74) *Attorney, Agent, or Firm* — Ostrolenk Faber LLP

(57) ABSTRACT

The invention relates to a method for enzyme cleavage of polysaccharides comprising a first sequence [→4)-β-D-GlcpA-(1→4)-α-L-Rhap3 sulphate-(1→]$_n$ and a second sequence [→4)-α-L-IdopA-(1→4)-α-L-Rhap3 sulphate-(1→]$_m$, the first and second sequences respectively comprising two monosaccharide units connected by an osidic bond, wherein said method is such that: said polysaccharide sequences are provided; a microorganism capable of producing an enzyme substance of the lyase class is provided; and said enzyme substance is brought into contact with said polysaccharide sequences in such a way as to bring about cleavage of the osidic bond according to a β-elimination reaction. The invention is characterized in that a microorganism belonging to the bacteria of the *Ochrobactrum* genus is chosen for producing said enzyme substance.

18 Claims, 4 Drawing Sheets

METHOD OF ENZYME CLEAVAGE OF POLYSACCHARIDES DERIVED FROM ALGAE

CROSS REFERENCE TO RELATED APPLICATIONS

The present application is a 35 U.S.C. §371 National Phase conversion of PCT/FR2008/000881, filed Jun. 23, 2008, which claims benefit of French Application No. 0704494, filed Jun. 22, 2007, the disclosure of which is incorporated herein by reference. The PCT International Application was published in the French language.

TECHNICAL FIELD

The present invention relates to a method of enzymatic cleavage of polysaccharides extracted from algae of the genus *Ulva*.

BACKGROUND

The polysaccharides are polymers and they constitute the essential elements of the green algae of the genus *Ulva*. Moreover, these green algae are very widely distributed on the coasts of all the continents and consequently are widely available at low cost.

These polymers are called "ulvan" and they contain acidic monosaccharides, notably glucuronic acid (GlcpA) and iduronic acid (IdopA) as well as neutral monosaccharides including rhamnose (Rhap), galactose (Galp), glucose (Glcp) and xylose (Xylp). Moreover, in these polymers, the rhamnose is substituted with a sulfate group on carbon 3, which will be called rhamnose 3 sulfate (Rhap3S).

These polymers contain interesting compounds, in particular iduronic acid and rhamnose 3 sulfate, notably for therapeutic or cosmetic applications.

However, the monosaccharides of these polymers are linked together relatively randomly, so that it is difficult to extract a relatively homogeneous composition. However, two main sequences, called aldobiuronic acids, including said compounds of interest, have been identified, a first sequence $[\rightarrow 4)$-$\beta$-D-GlcpA-$(1\rightarrow 4)$-$\alpha$-L-Rhap3 sulfate-$(1\rightarrow)]_n$ and a second sequence $[\rightarrow 4)$-$\alpha$-L-IdopA-$(1\rightarrow 4)$-$\alpha$-L-Rhap3 sulfate-$(1\rightarrow)]_m$. Sequences containing glucuronic acid chains, i.e.: $[\rightarrow 4)$-$\beta$-D-GlcpA-$(1\rightarrow 4)$-$\beta$-D-GlcpA-$(1\rightarrow)]_x$ have also been described; these glucuronan sequences can be integrated in the 2 main sequences constituted of the aforementioned aldobiuronic acids. However, although it has not been proved, these glucuronan sequences might also be present on a polymer other than ulvan, but extracted from the alga at the same time as the polymer constituted predominantly of sequences of aldobiuronic acids.

These compounds are comparable, respectively, to the glycosaminoglycans, notably heparin and heparan sulfate, and to chondroitin sulfate and dermatan sulfate.

However, as interesting as they might be, these polymers extracted from green algae are too heterogeneous to be used and incorporated as they are in pharmaceutical or cosmetic preparations. Accordingly, their fractionation into elementary compounds by means of specific enzyme compositions has been considered.

Thus, a first enzyme in the class of the lyases, glucuronan lyase, has already been identified, and it is active in cleaving the glucuronan sequences present in polysaccharides of the ulvan type. Moreover, this enzyme is obtained from a fungal microorganism, in particular from the strain *Trichoderma* CNCM I-3400. Reference may be made to document FR 2 885 911, which describes this microorganism for breaking down the glucuronan sequences of polysaccharides.

However, this enzyme composition does not actually permit cleavage of the aforementioned main sequences constituted of aldobiuronic acids, the result of which would be of interest.

Nevertheless, another enzyme composition in the class of the lyases is known, ulvan lyase, which makes it possible, a priori, to cleave the first and second sequences of the aforementioned aldobiuronic acids at the glycoside bonds, between units Rhap3 sulfate and GlcpA on the one hand, and between units Rhap3 and IdopA on the other hand, and according to a reaction of $\beta$ elimination.

This enzyme composition is described in the work of M. Lahaye et al. (*Carbohydrate Research* 1997, 304: 325-333) and it is derived from a marine bacterium. It makes it possible to fractionate the polymers of ulvan into oligomers.

However, the enzyme composition described in that work and notably its enzymatic activity relative to the substrate comprising ulvan polymers is relatively weak, and furthermore, it decreases rapidly as degradation proceeds, so that it is necessary to reintroduce enzymes of said enzyme composition for degradation to continue. In fact, the work cited above states that the degradation of ulvan by the isolated enzyme extract is slow and quickly reaches a plateau. Thus, it is described there that the increase in reducing sugars on ulvan submitted to degradation by the enzyme, said increase logically being identical to that of the sugars in the nonreducing terminal position, is 7.1% relative to the content of these sugars before incubation in the presence of the enzyme; furthermore, this degradation obtained in 200 minutes requires repeated additions of enzyme, on average every 25 minutes, to compensate the inactivation of the enzyme by degradation products. Consequently, use of this enzyme composition cannot be considered for industrial production of oligomers with uniform compositions and molecular weight, as the cost of obtaining these oligomers would be prohibitive.

Thus, a problem that arises, and that the present invention aims to solve, is to provide, according to a first aspect, a method of enzymatic cleavage that would make it possible not only to cleave the ulvan polymers between units Rhap3 sulfate and GlcpA, and between units Rhap3 and IdopA, but that would also make it possible to do so with a productivity enabling the oligomers of reduced size to be obtained cost-effectively.

SUMMARY

With the aim of solving this problem, the present invention proposes a method of enzymatic cleavage of polysaccharides comprising a first sequence $[\rightarrow 4)$-$\beta$-D-GlcpA-$(1\rightarrow 4)$-$\alpha$-L-Rhap3 sulfate-$(1\rightarrow)]_n$ and a second sequence $[\rightarrow 4)$-$\alpha$-L-IdopA-$(1\rightarrow 4)$-$\alpha$-L-Rhap3 sulfate-$(1\rightarrow)]_m$, the first and the second sequences being constituted respectively of two monosaccharide units joined by a glycoside bond, said method being of the type according to which: said polysaccharide sequences are supplied; a microorganism able to produce an enzymatic substance in the class of the lyases is supplied; and said enzymatic substance is brought in contact with said polysaccharide sequences so as to cause cleavage of the glycoside bond according to a reaction of $\beta$ elimination, according to the schematic mechanism:

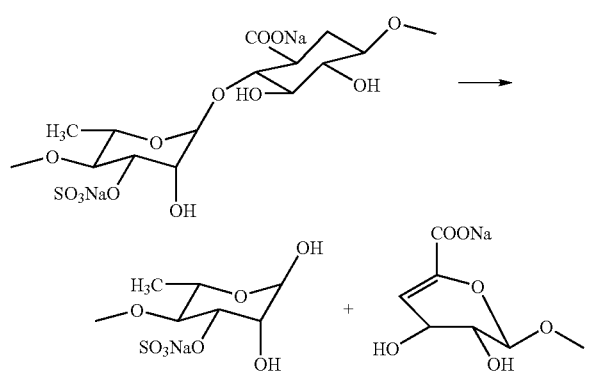

According to the invention, a microorganism belonging to the bacteria of the genus *Ochrobactrum* is selected for producing said enzymatic substance.

Thus, one characteristic of the invention resides in the detection of these bacteria of the genus *Ochrobactrum*, which produce an enzymatic substance that is specifically able to cleave the glycoside bond by β elimination but without leading to the appearance of degradation products that would actually interfere with the enzymatic activity; and this, in contrast to the enzymatic substances described in the prior art, and derived from marine bacteria, whose enzymatic activity is very rapidly interrupted, and for which it is then necessary to introduce fresh enzymatic substances into the reaction mixture, so that degradation continues.

Moreover, β elimination corresponds to cleavage of the glycoside bond on a glycoside sequence generating 2 fragments of saccharide molecules and causing the appearance, at the non-reducing terminal end created, of a heterocycle having an ethylene bond between carbon 4 and carbon 5, with the residue at the non-reducing terminal end corresponding to a 4-deoxy-(hex-4-ene) pyranosyluronic acid. Moreover, as will be explained below, owing to the appearance of this ethylene bond, the reaction velocity can easily be measured in UV spectroscopy, between 230 and 240 nm and more precisely at 235 nm.

Also, it will be observed that cleavage between units Rhap3 sulfate and GlcpA, and between units Rhap3 and IdopA, leads to exactly the same reaction products, even though on the one hand, for the first sequence we have glucuronic acid in the polymer, but on the other hand for the second sequence we have iduronic acid. This is because these two acids only differ in the configuration of their carbon 5. Thus, since carbon 5 is initially $sp^3$ hybridized and then becomes $sp^2$ hybridized after the reaction of β elimination, only one configuration is possible.

Thus, the enzymatic substance obtained by means of the bacterium of the genus *Ochrobactrum* not only makes it possible to obtain oligomers of low molecular weight at higher productivity than the enzymatic substances obtained with marine bacteria, but in addition the method according to the invention makes it possible to obtain homogeneous oligomers at high productivity.

BRIEF DESCRIPTION OF THE DRAWINGS

Other special features and advantages of the invention will become clear on reading the following description of particular examples of application of the invention, given by way of illustration but nonlimiting, referring to the appended drawings, where.

Figure 1:
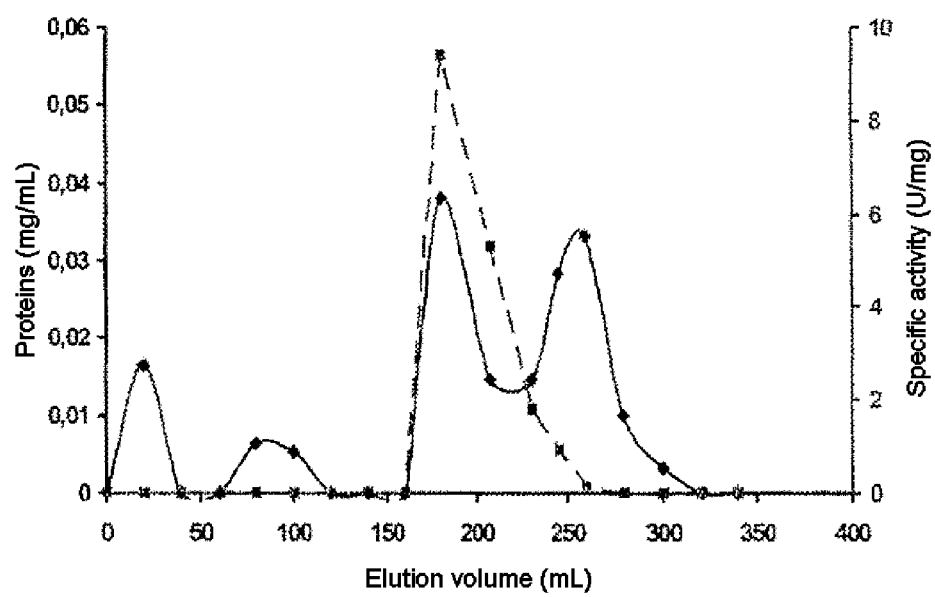
FIG. 1 is a diagram showing specific enzymatic activity of different elements of an enzymatic substance.

Particularly advantageously, the bacterial strain selected belongs to the species *Ochrobactrum tritici*, which is present in the soil. More precisely, this bacterial strain designated PEC.2 has the CNCM reference I-3776, duly deposited and registered with the National Collection of Cultures of Microorganisms (Collection Nationale de Cultures de Microorganismes, CNCM) at the Institut Pasteur, 25 rue du Docteur Roux, F-75724 Paris cedex 15.

DETAILED DESCRIPTION

According to a preferred embodiment of the invention, said bacteria are incubated with a polysaccharide substrate so as to produce said enzymatic substance, and then the incubated bacteria are isolated from said enzymatic substance in order to use the latter for producing the required oligomers.

Advantageously, said enzymatic substance is purified after the bacteria have been incubated, so as to retain exclusively the enzyme specific to cleavage of the glycoside bond. Thus, the enzymatic activity of the enzymatic substance which then only contains the enzyme, is then optimal with respect to the number of molecules cleaved per minute, and per amount of said enzymatic substance.

Preferably, moreover, the enzymatic substance obtained by means of the bacterial strain of the species *Ochrobactrum* causes cleavage of a number of glycoside bonds of said polysaccharide sequences between $6 \cdot 10^{16}$ and $6 \cdot 10^{20}$ per minute and per milligram of said enzymatic substance, for example between $6 \cdot 10^{17}$ and $6 \cdot 10^{19}$, and even more precisely, $6 \cdot 10^{18}$. As will be explained below, this enzymatic activity corresponds to approximately 10 U/mg, according to the usual measure; here, one U of enzyme represents the amount of enzyme extract that leads to the appearance of one micromole of 4-deoxy-(hex-4-ene) pyranosyluronic acid.

According to another preferred embodiment of the invention, as said polysaccharides additionally comprise glucuronan sequences within the sequences of aldobiuronic acids but also, very probably, glucuronan in the form of a separate polymer extracted at the same time as the polymer rich in aldobiuronic acids, said glucuronan is then eliminated. Thus, a polysaccharide is obtained containing essentially the two aldobiuronic acids and also containing the glucuronan sequences trapped in the sequences [→4)-β-D-GlcpA-(1→4)-α-L-Rhap3 sulfate-(1→]$_n$, [→4)-α-L-IdopA-(1→4)-α-L-Rhap3 sulfate-(1→]$_m$; however, the polysaccharide extracted from the alga is devoid of free glucuronan. As will be explained below, owing to this separation, the activity of ulvan lyase is promoted.

According to yet another preferred embodiment of the invention, said polysaccharides further comprise heparans and/or heparan sulfates including polymers constituted of [→4)-β-D-GlcpA-2-sulfate-(1→4)-α-D-GlcNsulfo-6-sulfate-(1→]$_x$ and/or [→4)-α-L-IdopA-2-sulfate (1→4)-α-D-GlcNsulfo-6-sulfate-(1→]$_y$.

Degradation of the polymer then makes it possible to obtain, depending on the amounts of enzyme used and the incubation time, oligomers of heparan and of heparan sulfate with a low degree of polymerization.

According to another aspect, the present invention relates to an enzymatic substance suitable for the method of enzymatic cleavage described above, said enzymatic substance being obtained from a microorganism belonging to the bacteria of the genus *Ochrobactrum*. More precisely said bacteria belong to the species *Ochrobactrum tritici*, the registered strain of which has the CNCM reference I-3776.

According to yet another aspect, the present invention also relates to cleaved polysaccharides obtained by a method of enzymatic cleavage of the type described above. Thus, according to a final aspect, the invention relates to the use of cleaved polysaccharides as mentioned above, for the application of a cosmetic preparation. The use of cleaved polysaccharides for the application of a therapeutic preparation is also envisaged. In addition, the application of cleaved polysaccharides for the application of a plant protection preparation is also envisaged.

Advantageously, a substrate will be selected that includes sequences of polysaccharides derived from an alga of the genus *Ulva* and called ulvan. These polysaccharide sequences of the ulvan type notably comprise a first sequence [→4)-β-D-GlcpA-(1→4)-α-L-Rhap3 sulfate-(1→]$_n$ and a second sequence [→4)-α-L-IdopA-(1→4)-α-L-Rhap3 sulfate-(1→]$_m$.

These ulvan polymers are depleted of glucuronan to optimize the production of the ulvan lyase activity. However, for certain applications, ulvan polymers containing glucuronan will be degraded enzymatically.

Before describing this method of separation, we shall describe the method of preparation of a bacterial strain of the species *Ochrobactrum tritici* PEC2 and in particular the strain bearing the CNCM reference I-3776, which is able to produce an enzymatic substance, namely an ulvan lyase. This ulvan lyase is able to cause cleavage of the glycoside bond according to a reaction of β elimination, between Rhap3 sulfate and GlcpA units, and between Rhap3 and IdopA units, respectively, of the first and second polysaccharide sequences mentioned above, according to the reaction scheme:

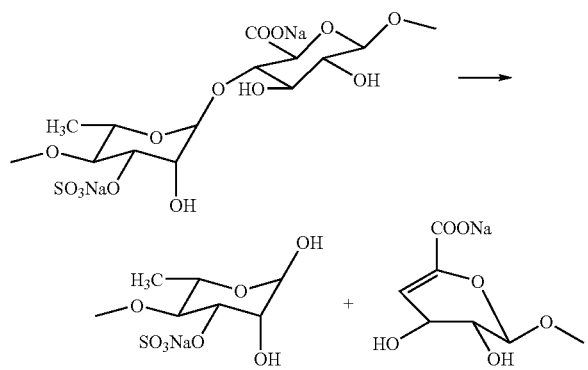

This strain is cultivated on a minimal mineral nutrient medium containing: NaCl, 22 g; Na$_2$SO$_4$, 3.7 g; KCl, 0.6 g; KBr, 0.1 g; MgCl$_2$.6H$_2$O, 10 g; CaCl$_2$.2H$_2$O, 2.94 g; NaHCO$_3$, 0.16 g; NaNO$_3$, 25 mg; NaH$_3$PO$_4$.12H$_2$O, 5 mg and H$_2$O q.s.f. 1 L; the pH is then 7.2. Ulvan (2 g/L) is added to the nutrient medium and it then constitutes the only source of carbon.

The strain that is able to degrade ulvan is isolated in a Petri dish containing the same nutrient medium with agar added. After incubation, the colonies that have developed most are collected. Quite obviously, the strains that metabolize the substrate by degrading it by β elimination are retained.

We shall now describe the method of separating the glucuronan and the ulvan substrate. For this, starting from an extract obtained by hot extraction of polymers from ulva and after removing the insoluble matter, the pH of the extract is lowered to 2 in the presence of dilute acid. In this way, a precipitate P including residues of glucuronic acid is obtained and the solution S that is recovered is adjusted to a neutral pH of about 7. This recovered solution S is then concentrated, purified for example by ultrafiltration, and then lyophilized or precipitated with alcohol. Thus, a polymer P2 is obtained including essentially sequences of aldobiuronic acids, and the glucuronan sequences that remain are those that are integrated in the main sequences.

Precipitate P, containing residues of glucuronic acid, can be treated to obtain unsubstituted glucuronan. Such a polymer finds applications in many sectors of industry.

Advantageously, the mixture of polymers P2 is used as substrate for growing the strain of *Ochrobactrum* PEC2 and for inducing the production of the "ulvan lyase" enzyme, which will cleave specifically, by the method of β elimination, on the one hand the bond between Rhap3S (rhamnose 3 sulfate) and GlcpA (glucuronic acid) of the first sequence of aldobiuronic acid, corresponding to the sequence [→4)-α-L-Rhap3 sulfate-(1→4)-β-D-GlcpA-(1→]$_n$ and on the other hand, the bond between Rhap3S (rhamnose 3 sulfate) and IdopA (iduronic acid) of the second sequence of aldobiuronic acid corresponding to the sequence [→4)-α-L-Rhap3 sulfate-(1→4)-α-L-IdopA-(1→]$_m$.

We shall now describe the method of preparation of the enzymatic activity. The strain of *Ochrobactrum tritici* PEC2 is first inoculated in a bioreactor with a capacity of 2 liters, filled with 1.5 L of mineral medium: NaCl 22 g; Na$_2$SO$_4$ 3.7 g; KCl 0.6 g; KBr 0.1 g; MgCl$_2$.7H$_2$O 5 mg; NaNO$_3$ 25 mg; NaH$_3$PO$_4$.12H$_2$O, H$_2$O q.s.f. 1 L, adjusted to pH 7.2 and with addition of yeast extract: 1 g/L, peptone: 5 g/L and ulvan polymers, preferably ulvan enriched with aldobiuronic acids (2 g/L).

Incubation is preferably carried out between 25 and 35° C., for example 30° C., stirring for an average time of 48 hours. During incubation, the concentration of ulvan lyase in the culture medium of the strain *Ochrobactrum tritici* PEC2 increased, and consequently the enzymatic activity of the culture medium also increased. Thus, the culture medium used as it is already provides degradation of the ulvan in oligomers after the bacterium has been removed by filtration or centrifugation. Advantageously, the bacteria are removed from the medium by centrifugation of the culture medium at 30 000 g for about 30 min.

The ulvan lyase is concentrated and purified according to 3 levels of purification. A first level A of preparation of the enzyme corresponds to the culture medium from which the bacteria were removed after incubation.

A second level of preparation B is obtained firstly by adding ammonium sulfate (60% w/v) to the culture medium obtained from the first level A of preparation, to precipitate the proteins that it contains. The proteins include, of course, the enzyme ulvan lyase. Then, the precipitated culture medium is centrifuged at 30 000 g for 30 minutes and the protein pellet is recovered. Finally, the protein pellet is resuspended in about 10 ml of a buffer solution Tris/HCl 20 mM at pH 7.5.

A third level of purification C is obtained by chromatographic fractionation of the result of the treatment at the second level B on anion-exchange resin, for example in a DEAE-methacrylate column, and recovering exclusively the fraction corresponding to ulvan lyase.

Now regarding the activity of the enzyme preparations, they are measured by the value U (unit), which corresponds to the amount of enzyme extract that leads to the appearance of one micromole (μM) of molecules of 4-deoxy-(hex-4-ene) pyranosyluronic acid per minute, or approximately $6 \cdot 10^{17}$ molecules.

The appearance of the latter compound is measured by UV spectroscopy at a wavelength between 230 and 240 nm and more precisely at 235 nm, which makes it possible to visualize the appearance of the double bond. Also, the value of one unit U corresponds to $6 \cdot 10^{17}$ glycoside bonds cleaved. Moreover, the molar extinction coefficient ε is 5000 L/mol/cm, making it possible to calculate the concentrations by application of the Beer-Lambert law, after measuring the absorption.

The specific activity corresponds to the number of μM of molecules of 4-deoxy-(hex-4-ene)pyranosyluronic acid formed per minute and per milligram of proteins.

FIG. 1 shows the elution profile, in semi-preparative anion-exchange chromatography in a DEAE-methacrylate column, of the proteins present in the culture medium of the strain *Ochrobactrum tritici* PEC2. The eluent is Tris-HCl 0.02 M, at pH=8.5, and with NaCl gradient. As can be seen from FIG. 1, with the curve shown as a continuous line representing the elution of the various proteins obtained from the culture medium, precipitated with ammonium sulfate and then purified by anion-exchange chromatography, and the curve shown as a dashed line representing the specific enzymatic activity, the specific enzymes of the ulvan lyase activity can easily be collected according to the third level of purification C mentioned above. Of course, the elution volume plotted on the abscissa corresponds to the time for passage of the proteins through the column, said time being discriminating for the enzyme ulvan lyase; whereas the specific activity is obtained by measuring the absorbance, at 235 nm, of the product of elution put in contact with an ulvan substrate.

Moreover, the following table shows, in addition to the activity and the characteristics of the proteins obtained at the third level C of preparation, those of the proteins obtained according to the other two levels of purification A and B.

TABLE

| Levels of purification | Total proteins (mg) | Total activity U | Specific activity (U/mg) | Yield % | Purification factor |
|---|---|---|---|---|---|
| Culture medium without bacteria (A) | 130 | 15.65 | 0.12 | 100 | 1 |
| Precipitation with (NH$_4$)$_2$SO$_4$ (B) | 20.76 | 10.7 | 0.515 | 16 | 43 |
| Purification by chromatography (C) | 0.76 | 7.20 | 9.48 | 0.6 | 80 |

It can be seen that the specific activity of the substance or enzyme preparation resulting from the first level A of preparation and containing all of the proteins present in the culture medium of the strain *Ochrobactrum* PEC.2, after removal of the bacteria, is approximately 100 times lower than the specific activity of the enzymatic substance comprising exclusively ulvan lyase. Moreover, it will be noted that the second level of purification B makes it possible to obtain a specific activity almost five times greater than the specific activity of the incubation medium of the strain of *Ochrobactrum* after removal only of the bacteria.

It is also necessary to calculate the costs of purification of the culture medium according to the three levels, for proper appreciation of the productivity of degradation of the polysaccharides.

EXAMPLES

The following examples are provided only for the purpose if illustrating the invention and are not to be construed as limiting.

Example 1

Figure 2:
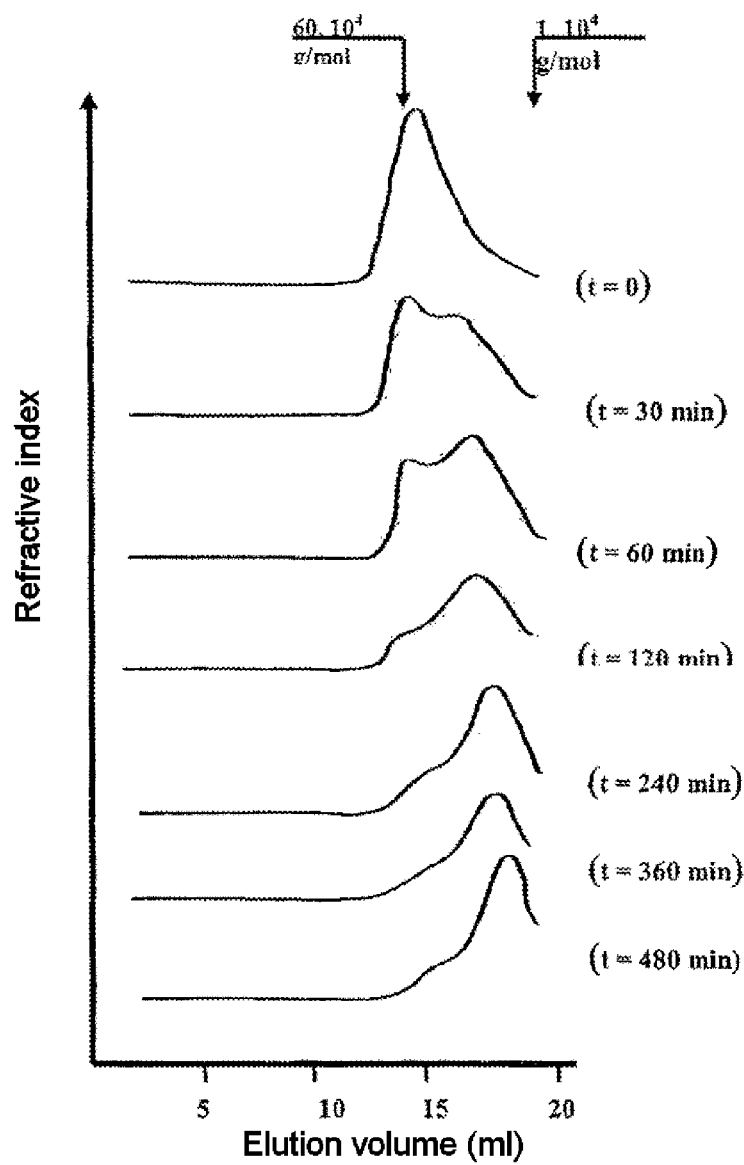
FIG. 2 is a graph showing measurement of the enzymatic activity of said enzymatic substance.

Measurements of the rate of enzymatic degradation will be illustrated in this example, referring to FIG. 2.

An enzyme preparation obtained according to the third level of purification C (0.5 U) is applied to 100 mL of a solution of substrate at 2 g/L, the substrate corresponding to ulvan constituted essentially of aldobiuronic acids. This substrate is in fact obtained by removing glucuronans from it, according to the method described above.

The average molecular weight of the ulvan used as substrate is determined by steric exclusion chromatography coupled to a light diffusion detector in line with a refractometer (SEC-MALLS technology, standing for Size Exclusion Chromatography Coupled to Multi-angle Laser-Light Scattering); said average molecular weight is $6 \cdot 10^5$.

The degradation experiment is carried out at 30° C. for a total time of 8 hours, and as shown in FIG. 2, it is followed by analysis of the molecular weight of the ulvan by SEC-MALLS, at the start of the experiment, t=0; a half-hour and an hour after, t=30 minutes and t=60 minutes; two hours after, t=120 minutes; four hours after, t=240 minutes; six hours after, t=360 minutes and finally eight hours after, t=480 minutes.

At the start of the experiment, t=0, the average molar mass of the sample is therefore $6 \cdot 10^5$ g/mol and fractions of low molar mass are detected notably starting from the incubation time t=120 min. This reveals the degradation of the substrate by endoglycosidase activity.

After 8 hours of incubation, ulvan of high molar mass of $6 \cdot 10^5$ g/mol, corresponding to the initial substrate, is no longer detected.

The evolution of the chromatographic profile according to the SEC-MALLS technology shows that it is possible to obtain fractions of ulvan whose average molar mass will depend on the incubation time of the enzyme in the presence of the substrate. The average degree of polymerization of the ulvan oligomers is adjusted according to the incubation time and the concentration of enzyme added once at the moment of constitution of the reaction mixture. For an incubation time of 8 hours, the oligomers obtained have a degree of polymerization essentially between 2 and 25.

Example 2

Figure 3:
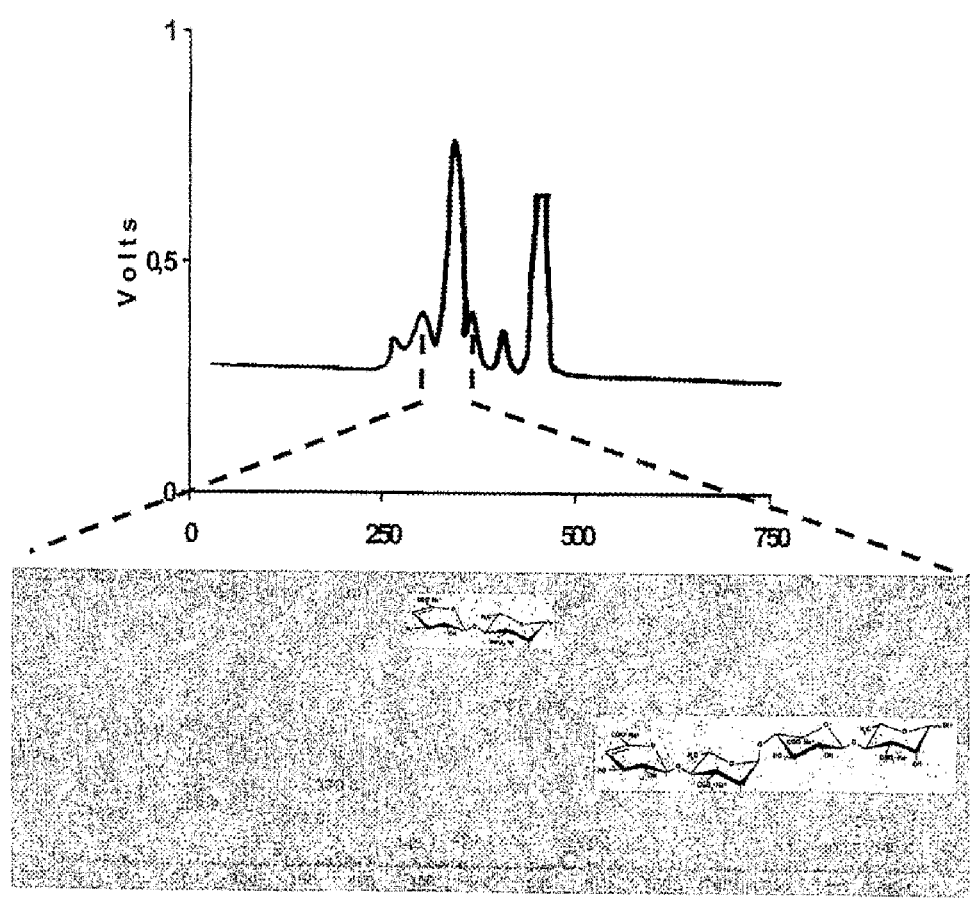
FIG. 3 shows two superposed spectra, corresponding to degradation products of the enzymatic activity according to a first embodiment, one obtained by steric exclusion chromatography on Biogel P2, and the other, below, obtained by mass spectroscopy; and, FIG. 4 shows a spectrum obtained by steric exclusion chromatography on Biogel P6, corresponding to degradation products of the enzymatic activity according to a second embodiment.

According to example 2, oligomers with a degree of polymerization DP essentially equivalent to 2 are produced in accordance with the method of enzymatic cleavage according to the invention. The method of obtaining these oligomers will be described first, and then reference will be made to FIG. 3, illustrating an elution profile and, at the bottom, a corresponding mass spectrum of said oligomers.

After incubating, for 72 hours at 30° C., a preparation of 100 ml constituted of ulvan enriched with aldobiuronic acids at a rate of 20 g/L, and with addition of the enzyme preparation obtained at the third level of purification C (1 U of purified extract C) once at the moment of constitution of the mixture, the mixture is heated at 100° C., for example for five minutes, to inactivate the enzyme. Then the product is filtered on a filter with pore size of 0.2 μm to remove the denatured proteins. Then isopropanol (2v) is added to the preparation to precipitate the saccharide compounds with molecular weight greater than 2000 Da (g/mol) and that had not been degraded by the enzyme. The compounds precipitated are recovered after centrifugation, for example at 30 000 g for 30 minutes, and then they are lyophilized. The supernatant is submitted to evaporation to remove the isopropanol and concentrate the sample, which is lyophilized in its turn.

The yield in degradation is found after measuring the mass of the products present in the precipitate and in the supernatant. In this example 2, 65% of oligomers of ulvan with a low degree of polymerization are recovered from the supernatant; 35% of the starting ulvan had not been degraded to small molecules. Analysis of the product resulting from degradation by steric exclusion chromatography on Biogel P2 (detection by refractometry) reveals degradation of 65% of the initial substrate to small molecules. As shown in FIG. 3, the main fraction eluted between 310 and 380 ml, around 360 ml, is analyzed by mass spectrometry of the ESI-Q/TOF type (electrospray-quadrupole-time of flight). The results show that 80% of the oligomers resulting from degradation of the ulvan have a degree of polymerization DP equal to 2, the ion having a mass of 401.1, whereas 20% of the oligomers have a degree of polymerization DP equal to 4, the ion having a mass of 824.8.

Example 3

According to example 3, oligomers with a degree of polymerization DP essentially greater than 2 are produced.

To do this, incubation of the enzyme (preparation C, 1 U) in the presence of 100 ml of the ulvan substrate enriched with aldobiuronic acids at a rate of 20 g/L is in this case continued for 36 hours.

Figure 4:
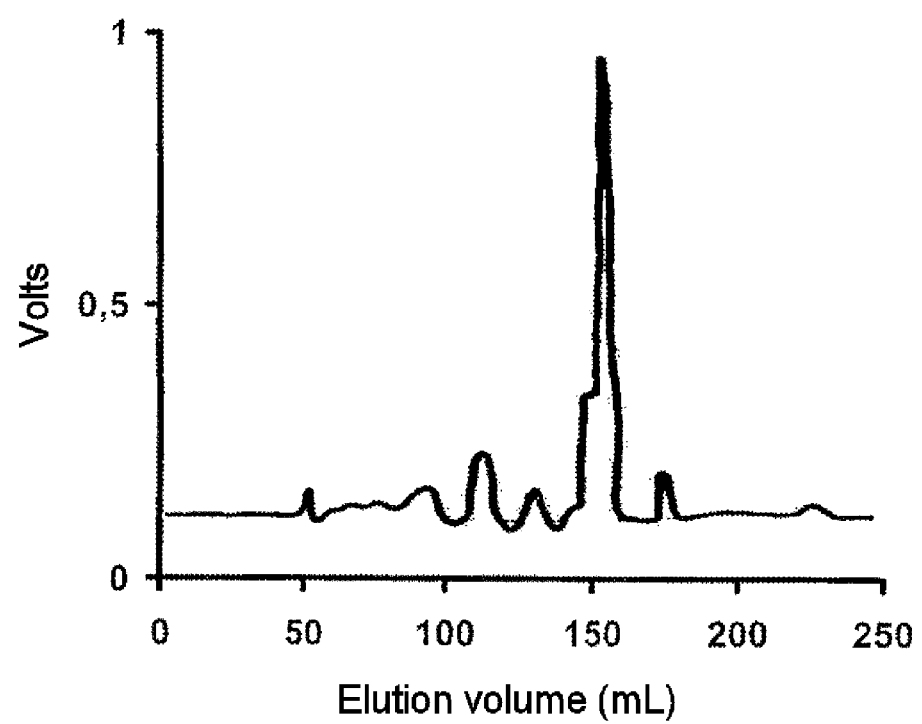

Elution on a Biogel P6 column reveals the presence of oligomers, eluted between 60 and 170 ml, as shown by the elution profile presented in FIG. 4. More precisely, we find oligomers of small size or with a lower degree of polymerization DP, eluted later, between 150 and 170 ml, as well as larger oligomers with a degree of polymerization greater than 4, eluted between 60 and 140 ml. Thus, this demonstrates that it is possible to obtain oligomers of ulvan of the desired size notably by varying the parameters of incubation time and amount of enzymatic substance.

Of course, these results obtained on modest amounts of raw materials, whether enzymatic substance or ulvan substrate, can easily be transferred to industrial quantities, for the purpose of producing the desired oligomers at advantageous costs.

The production of oligosaccharides derived from ulvans enriched with aldobiuronic acids is not mentioned in the prior art. The oligosaccharides according to the prior art have degrees of polymerization DP of 2 or 4 and exceptionally 8, as few oligomers are produced by the methods described and only the main ones have been described.

In the method according to the invention, the oligomers are predominantly composed of aldobiuronic acids as said method makes it possible to remove the glucuronan present in the raw extract. It also allows the size of the desired oligomers to be adjusted, i.e. with a degree of polymerization DP of 2 or 4 predominantly by degradation of the polymer enriched with aldobiuronic acids for 72 h. In this case, we obtain a yield of 65% of oligomers with DP 2 and DP 4, and 35% of the product resulting from the degradation has a degree of polymerization DP greater than 4.

In the case of degradation for 36 h, few oligomers of DP 2 are formed, and most of the oligomers have a DP>4, as shown in FIG. 4. The size of the ulvan oligomers can be varied according to the conditions of incubation of the ulvan substrate in the presence of the enzyme produced by *Ochrobactrum*. In 8 h of incubation, the polymer with average molecular weight of $6 \cdot 10^5$ Da is degraded to oligomers with DP mainly between 2 and 25.

It is therefore possible, by the method described here, to vary the average DP of the ulvan oligomers enriched with aldobiuronic acids. Moreover, families constituted of oligomers with closer degrees of polymerization DP can be obtained, either oligomers with DP 2, 4, or oligomers whose DP is between 2 and 8; or oligomers whose DP is between 2 and 25 and between 4 and 25 by extraction of the oligomers with DP equal to 2. Methods of nanofiltration or methods of chromatography will be used for these purifications.

The oligomers obtained are thus comparable to the glycosaminoglycans, notably heparin and heparan sulfate, and to chondroitin sulfate and dermatan sulfate. Therefore they find application in the therapeutic and cosmetic fields.

Thus, applications of the ulvan oligosaccharides in the cosmetic area are envisaged, notably for treating the skin against lesions caused by the environment and by aging, and for protecting and improving the appearance and the physiological state of the skin. The use of ulvan oligosaccharides for modulating the adhesion and proliferation of tumor cells is also envisaged.

Applications in the crop protection area are also envisaged; for example as agent for fertilization of plants. Compositions from the families of oligomers with degree of polymerization DP between 2 and 25 and enriched with aldobiuronic acids are also envisaged for stimulating the natural defenses of plants against biotic and abiotic stresses.

What is claimed is:

1. A method of enzymatic cleavage of polysaccharides comprising a first sequence $[\rightarrow 4)\text{-}\beta\text{-D-GlcpA-}(1\rightarrow 4)\text{-}\alpha\text{-L-Rhap3 sulfate-}(1\rightarrow)]_n$ and a second sequence $[\rightarrow 4)\text{-}\alpha\text{-L-IdopA-}(1\rightarrow 4)\text{-}\alpha\text{-L-Rhap3 sulfate-}(1\rightarrow)]_m$, the first and the second sequences being respectively constituted of two monosaccharide units joined by a glycoside bond, comprising:

supplying a solution of ulvan polysaccharides having said first sequence and said second sequence;

supplying a genus *Ochrobactrum* microorganism able to produce an enzymatic substance of the class of the lyases which are adapted to cause cleavage of the glycoside bond according to a reaction of β elimination, according to the schematic mechanism:

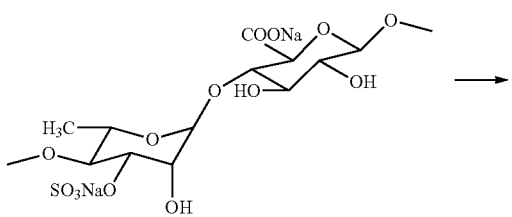

-continued

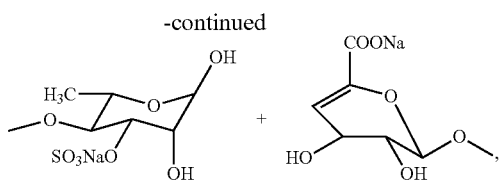

said enzymatic substance having an enzymatic activity which is tolerant of an increase in degradation products in the solution; and contacting the enzymatic substance with the ulvan polysaccharides under such conditions that the enzymatic substance is effective to cause said cleavage substantially without loss of enzymatic activity due to a production of polysaccharide degradation products.

2. The method of enzymatic cleavage as claimed in claim 1, wherein the microorganism belongs to the species *Ochrobactrum tritici*.

3. The method of enzymatic cleavage as claimed in claim 1 wherein the microorganism is incubated with a polysaccharide substrate to produce said enzymatic substance, and wherein the incubated microorganism is isolated from said enzymatic substance.

4. The method of enzymatic cleavage as claimed in claim 3, wherein said enzymatic substance is purified so that it retains at least an enzyme specific to cleavage of the glycoside bond.

5. The method of enzymatic cleavage as claimed in claim 1, wherein the enzymatic substance causes the cleavage of a number of glycoside bonds of said polysaccharide sequences between $6\times10^{16}$ and $6\times10^{20}$ per minute and per milligram of said enzymatic substance.

6. The method of enzymatic cleavage as claimed in claim 1, wherein said ulvan polysaccharides are extracted from an alga of the genus *Ulva*.

7. The method of enzymatic cleavage as claimed in claim 6, wherein, said ulvan polysaccharides additionally comprise at least one sequence including glucuronan, and said sequence including glucuronan is removed from said first and second sequences $[\rightarrow 4)\text{-}\beta\text{-D-GlcpA-}(1\rightarrow 4)\text{-}\alpha\text{-L-Rhap3 sulfate-}(1\rightarrow]_n$, $[\rightarrow 4)\text{-}\alpha\text{-L-IdopA-}(1\rightarrow 4)\text{-}\alpha\text{-L-Rhap3 sulfate-}(1\rightarrow]_m$.

8. The method of enzymatic cleavage as claimed in claim 6, wherein said ulvan polysaccharides further comprise heparans including polymers constituted of $[\rightarrow 4)\text{-}\beta\text{-D-GlcpA-2-sulfate-}(1\rightarrow 4)\text{-}\alpha\text{-D-GlcNsulfo-6-sulfate-}(1\rightarrow]_x$ and/or $[\rightarrow 4)\text{-}\alpha\text{-L-IdopA-2-sulfate }(1\rightarrow 4)\text{-}\alpha\text{-D-GlcNsulfo-6-sulfate-}(1\rightarrow]_y$.

9. The method of enzymatic cleavage as claimed in claim 2, wherein the microorganism belongs to the strain *Ochrobactrum tritici* CNCM I-3776.

10. The method of enzymatic cleavage as claimed in claim 1, wherein oligomers formed as degradation products of said ulvan polysaccharides have a degree of polymerization between 2 and 25.

11. The method of enzymatic cleavage as claimed in claim 10, wherein said method comprises further comprising adding a cosmetic preparation to said oligomers.

12. The method of enzymatic cleavage as claimed in claim 10, wherein said method comprises further comprising adding a plant protective preparation to said oligomers.

13. The method of enzymatic cleavage as claimed in claim 10, further comprising adding a therapeutic preparation to said oligomers.

14. A method of enzymatic cleavage of polysaccharides comprising a first sequence $[\rightarrow 4)\text{-}\beta\text{-D-GlcpA-}(1\rightarrow 4)\text{-}\alpha\text{-L-Rhap3 sulfate-}(1\rightarrow]_n$ and a second sequence $[\rightarrow 4)\text{-}\alpha\text{-L-IdopA-}(1\rightarrow 4)\text{-}\alpha\text{-L-Rhap3 sulfate-}(1\rightarrow]_m$, the first and the second sequences being respectively constituted of two monosaccharide units joined by a glycoside bond, comprising:

supplying a solution of polysaccharides extracted from alga of the genus *Ulva* having said first sequence and said second sequence;

supplying an enzymatic substance corresponding to an ulvan lyase of a microorganism of genus *Ochrobactrum*, adapted to cause cleavage of the glycoside bond according to a reaction of β elimination substantially without self-inhibition by ulvan lyase degradation products of the polysaccharides at a level of at least 20 g/l, according to the schematic mechanism:

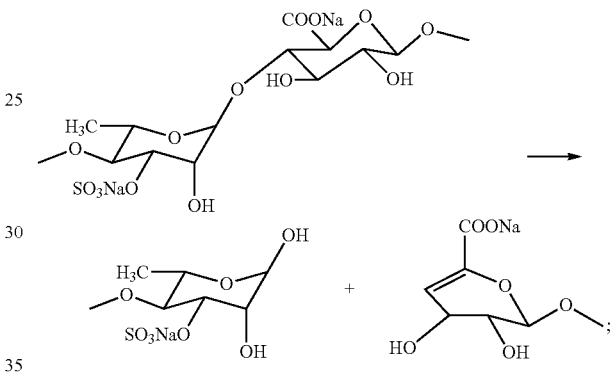

and degrading linkages of the first sequence to the second sequence within the polysaccharides with the enzymatic substance by β elimination.

15. The method of enzymatic cleavage as claimed in claim 14, wherein the enzyme substance is produced by a microorganism which belongs to the species *Ochrobactrum tritici*.

16. The method of enzymatic cleavage as claimed in claim 14, wherein the ulvan lyase degradation products of said polysaccharides are oligomers having a degree of polymerization between 2 and 25.

17. The method of enzymatic cleavage as claimed in claim 14, wherein the enzyme substance is produced by a process comprising incubating the microorganism with a polysaccharide substrate comprising said first sequence and said second sequence, and thereafter purifying the enzyme substance so as to substantially exclusively retain an ulvan lyase enzyme activity specific to cleavage of the glycoside bond.

18. The method of enzymatic cleavage as claimed in claim 14, wherein the enzymatic substance causes the cleavage of a number of glycoside bonds of said polysaccharide sequences between $6\times10^{16}$ and $6\times10^{20}$ per minute and per milligram of said enzymatic substance in the presence of at least about 20 g/l of said polysaccharides.

\* \* \* \* \*

UNITED STATES PATENT AND TRADEMARK OFFICE
CERTIFICATE OF CORRECTION

PATENT NO. : 8,563,276 B2  Page 1 of 1
APPLICATION NO. : 12/664743
DATED : October 22, 2013
INVENTOR(S) : El Boutachfaiti et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 563 days.

Signed and Sealed this

Fifteenth Day of September, 2015

Michelle K. Lee
*Director of the United States Patent and Trademark Office*